United States Patent [19]

Parker

[11] 4,366,331

[45] Dec. 28, 1982

[54] PROCESS FOR PRODUCTION OF 2,6-DI-TERT-ALKENYL PHENOLS

[75] Inventor: Dane K. Parker, Massillon, Ohio

[73] Assignee: The Goodyear Tire & Rubber Company, Akron, Ohio

[21] Appl. No.: 330,506

[22] Filed: Dec. 14, 1981

Related U.S. Application Data

[63] Continuation of Ser. No. 159,081, Jun. 13, 1980, abandoned.

[51] Int. Cl.$^3$ .................... C07C 37/11; C07C 39/06
[52] U.S. Cl. .................................. 568/785; 568/784
[58] Field of Search ............................. 568/785, 784

[56] References Cited

U.S. PATENT DOCUMENTS

| | | | |
|---|---|---|---|
| 2,161,826 | 6/1939 | Kyrides | 568/784 |
| 2,968,679 | 9/1961 | Aelony | 568/784 |
| 3,198,842 | 8/1965 | Berrigan | 568/784 |
| 3,526,668 | 9/1970 | Starnes | 568/784 |

OTHER PUBLICATIONS

Yamada et al., "Bull. Chem. Soc. of Japan", vol. 50(3) 750, (1977).

Regen, "Angewandte Chemie", Int. ed., vol. 18, No. 6, (6/1979), pp. 421-492.

Chiles, et al., "Tetrahedron Letters", No. 36, pp. 3367-3370, (1979).

"Chemistry and Properties of Crosslinked Polymers", Academic Press Ltd., (1979), edited by Labana.

*Primary Examiner*—Werren B. Lone
*Attorney, Agent, or Firm*—D. O. Nickey

[57] ABSTRACT

There is disclosed a process for the production of 2,6-di-tert-alkyl-4-alkenyl phenols wherein the improvement comprises the reaction of a 2,6-di-tert-alkyl phenol with an allyl halide to yield the 2,6-di-tert-alkyl-4-alkenyl phenol through the use of a triphase or polymer bound catalyst.

6 Claims, No Drawings

PROCESS FOR PRODUCTION OF 2,6-DI-TERT-ALKENYL PHENOLS

This is a continuation of application Ser. No. 159,081, filed June 13, 1980 now abandoned.

TECHNICAL FIELD

This invention relates to an improved method for the production of 2,6-di-t-alkyl-4-alkenyl phenols. More specifically, this invention relates to insoluble polymer bound catalysts for the production of 2,6-di-t-alkyl-4-alkenyl phenols.

BACKGROUND ART

Numerous processes for the allylation of alkyl phenols are known. U.S. Pat. No. 2,968,679 discloses a process wherein phenol is converted to sodium phenoxide followed by the reaction of a substantially anhydrous suspension of sodium phenoxide and finely divided sodium hydroxide with allyl chloride in a nonpolar solvent. This process suffers from poor yields and is not selective for alkylation at a specific site on the phenolic nucleus.

S. Yamada et al., *Bull. Chem. Soc. of Japan*, Vol. 50, (3) 750 (1977), discloses a reaction wherein phenols (phenol, hydroquinone, resorcinol, and o-cresol) are reacted with prenyl halides (3-methyl-2-butenyl chloride and geranyl chloride) in the presence of an alkali metal (Na) in ether. In these reactions, phenols with the corresponding prenyl group at the ortho position were obtained selectively.

U.S. Pat. No. 3,198,842 discloses a continuous process for the ortho-allylation of phenol by percolating a solution of β,γ-alkenyl halide in an anhydrous inert nonpolar hydrocarbon solvent through a solid alkali metal salt of a phenol at a temperature from 0° C. to 100° C.

U.S. Pat. No. 3,526,668 discloses a method for producing an allyl phenol which consists of contacting an alkali metal salt of a 2,6-disubstituted phenol with a primary allyl halide in an organic solvent at a temperature from 25° to 300° C. to form a 2,6-disubstituted p-allyl phenol.

The prior art does not disclose or suggest that a triphase catalyst can be used to produce 2,6-di-t-alkyl-4-alkenyl phenols. Those skilled in the art are constantly searching for new processes to produce 2,6-di-t-alkyl-4-alkenyl phenols since these compounds are valuable as chemical intermediates and antioxidants. The process of the present invention provides for the use of triphase catalysts that have the advantages over what is presently known in the art in that high yields are obtainable of a specific product, elimination of high cost solvents and reaction equipment, reuseable catalysts and easy work-up of the product.

Triphase catalysis is an unique form of heterogeneous catalysis in which the catalyst and each of a pair of reactants are located in separate phases. A discussion of triphase catalysis systems, their preparation and mechanisms can be found in Regen, S. L.; *Angewandte Chemie*, Int. Ed. Vol. 18, No. 6, (6–1979) pages 421–492, said publication is herein incorporated by reference.

The process of the present invention is limited to triphase catalysts wherein the catalytic resin is either a macroreticular or microreticular polystyrene resin modified so as to contain quaternary phosphonium or ammonium salts.

A review of functionalization of crosslinked polystyrene resins by chemical modification can be found in *Chemistry and Properties of Crosslinked Polymers*, Academic Press, Inc. Santokh S. Labana, Editor (1977), pages 59 et seq., said publication is herein incorporated by reference.

M. S. Chiles and P. C. Reeves in *Tetrahedron Letters* No. 36, pp. 3367–3370, Pergamon Press Ltd. (1979), disclose phase transfer catalysts anchored to polystyrene. More specifically, they teach that quaternary phosphonium and ammonium salts attached to polystyrene resins by short (2–3 atom) carbon chains are highly active phase transfer catalysts for a variety of nucleophilic substitution reactions. The synthetic utility of these catalysts was explored by examining the reactions of a variety of nucleophiles with 1-bromopentane under phase transfer conditions. Chiles and Reeves disclose nucleophilic substitution reactions described generally by the equation

wherein Nuc$^\ominus$ is selected from the group consisting of CN$^\ominus$, I$^\ominus$, Ph—O$^\ominus$, Ph—S$^\ominus$, N$_3^\ominus$, SCN$^\ominus$, S$^{\ominus 2}$, CH$_3$CO$_2^\ominus$; with reaction times ranging from 0.2 to 8.0 hours at a temperature of 110° C. and molar ratios of Nuc$^\ominus$/R-X/Cat. ranging from 1.5/1/.01 to 4/1/.01. However, Chiles and Reeves do not disclose or suggest the use of a triphase catalyst for the production of 2,6-di-tert-alkyl-4-alkenyl phenols. In fact, the procedure disclosed by Chiles and Reeves discloses a reaction wherein the final product is an ether and not para substitution of a dialkylated phenol.

DISCLOSURE OF INVENTION

There is disclosed a process wherein a 2,6-di-tert-alkyl phenol of the structural formula:

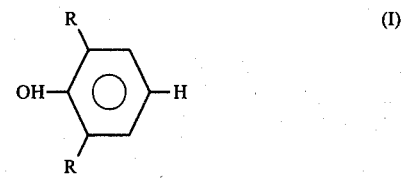

is reacted with an allyl halide of the structural formula:

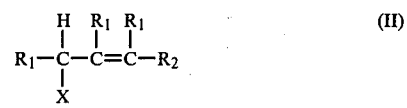

in the presence of an aqueous solution of an alkali metal hydroxide, a catalyst, and heat to yield a 2,6-di-t-alkyl-4-alkenyl phenol of the structural formula:

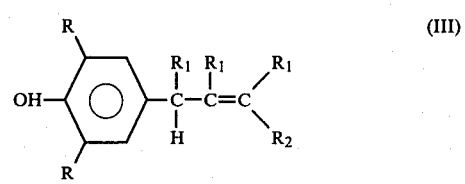

wherein R is a tertiary alkyl radical of 4 to 8 carbon atoms and $R_1$ is a monovalent radical selected from the group consisting of hydrogen, alkyl radicals of 1 to 6 carbon atoms; and $R_2$ is a monovalent radical selected from the group consisting of hydrogen, alkyl radicals of 1 to 6 carbon atoms and aryl radicals of 6 to 10 carbon atoms; and X is a chlorine or bromine radical, the improvement characterized in the use of a triphase catalyst defined by the formula:

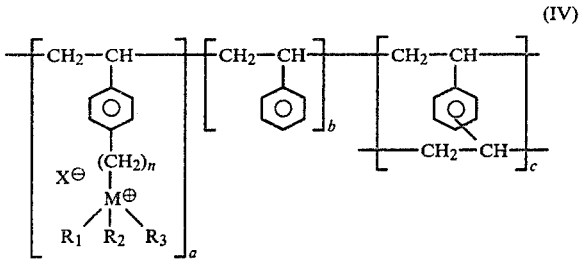

(IV)

wherein the ratio of a to b plus c may vary between 1 to 1 to 1 to 100 with a preferred range being 1 to 5 to 1 to 50 and wherein $R_1$, $R_2$ and $R_3$ are the same or different radicals selected from the group comprised of alkyl radicals of 1 to 12 carbon atoms, secondary alkyl radicals of 3 to 12 carbon atoms, cycloalkyl radicals of 5 to 8 carbon atoms; $X^\ominus$ is a radical selected from the group consisting of chlorine, fluorine and bromine and hydrogen sulfate radicals; M is phosphorus or nitrogen and n is equal to a whole positive integer from 1 to 12.

The basis of this invention resides in the use of triphase catalysts as described in structural formula (IV) in the preparation of compounds of formula (III).

The triphase or polymer bound catalysts of this invention may be easily prepared from polystyrene resins. Polystyrene resins are modified to contain reactive halogen functionalities and then quaternized by reaction with a tertiary phosphine or tertiary amine.

Representative of the compounds of structural formula (I) that can be used in the process of this invention are:
2,6-di-t-butyl-phenol
2,6-di-t-pentyl-phenol
2,6-di-t-heptyl-phenol Representative of the compounds of structural formula (II) that can be used in the process of the present invention are:
cinnamyl bromide
allyl chloride
allyl bromide
1-bromo-2-hexene
1-chloro-2-hexene
β-methylallyl bromide
β-methylallyl chloride Representative of the compounds of structural formula (III) that can be produced by the process of the present invention are:
2,6-di-t-butyl-4-(2-butenyl)phenol
2,6-di-t-butyl-4-(3-phenyl-2-propenyl)phenol
2,6-di-t-pentyl-4-(3-phenyl-2-propenyl)phenol
2,6-di-t-butyl-4-allyl phenol

PREPARATION OF RESIN BOUND PHOSPHONIUM CATALYST

To prepare a catalyst of general structural formula (IV) wherein M is phosphorus, a 1 liter 3 neck flask is charged with 50 grams (0.0625 moles) of chloromethylated 1% crosslinked polystyrene resin (marketed under the trade name Bio-Beads S-X1 by Bio-Rad Labs., hereinafter known as S-X1 resin) and 500 milliliters of dimethylformamide (hereinafter known as DMF). A mechanical stirrer is attached to the reaction flask and a slow purge of nitrogen was begun with stirring. 17.2 grams (0.085 moles) of $(C_4H_9)_3$ P was added to the reaction mixture by use of a long needle disposable syringe. Care must be exercised since $(C_4H_9)_3$ P is pyrophoric; a reaction hood and nitrogen atmosphere are suggested. After the $(C_4H_9)_3$ P was added to the reaction mixture all at once the reaction mixture was warmed to 130° C. with stirring for 4 hours. As the reaction proceeds the mixture becomes difficult to stir. After 4 hours of reaction time the mixture was cooled and filtered in a reaction hood. The filtrate was washed with DMF and then acetone and allowed to dry. The procedure just outlined can be summarized by the equation:

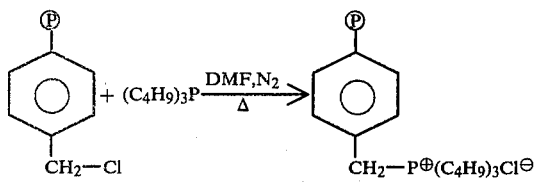

wherein the symbol ⓟ-is a shorthand representative of a crosslinked polystyrene matrix.

PREPARATION OF RESIN BOUND AMMONIUM CATALYST

To prepare a catalyst of general structural formula (IV) wherein M is nitrogen, a 1 liter 3 neck flask was charged with 20.0 grams (0.025 moles) of S-X1 resin, 26.9 grams (0.10 mol) of tri-n-hexyl amine and 150 ml. of $CH_3CN$. A condenser and mechanical stirrer was attached to the reaction vessel and boiling chips were added to the mixture. The reaction mixture was then heated to boiling and allowed to reflux overnight to yield 26.73 grams of polymer bound benzyl tri-n-hexyl ammonium chloride.

BEST MODE OF CARRYING OUT THE INVENTION

EXAMPLE I

Preparation of 2,6-di-t-butyl-4-allyl phenol by Quaternary Ammonium Triphase Catalysis To a 1 liter 3 neck flask equipped with a mechanical stirrer, thermometer, nitrogen inlet, dropping funnel and condenser was 40 grams (1.0 mole) of sodium hydroxide. The NaOH was dissolved in 50 ml. of $H_2O$ with stirring and then 100 ml. of toluene was added. To this mixture was then charged 6.4 grams ($\approx$0.006 mole) of quaternary ammonium S-X1 resin. The dropping funnel was then charged with a solution prepared from 51.5 grams (0.25 mole) 2,6-di-t-butyl phenol, 32.0 grams (0.264 mole) allyl bromide and 100 ml. of toluene. The reaction mixture of NaOH, toluene and catalyst within the 3-neck flask was heated to 50°–60° C. under a nitrogen blanket with stirring before addition of the 2,6-di-t-butyl phenol and allyl bromide solution was begun. Addition of the 2,6-di-t-butyl phenol and allyl bromide solution was completed within 40 minutes as the temperature increased to 70°–74° C. Stirring was continued for 1 hour after addition was completed and then 100 ml. of toluene and 100 ml. of H₂O was added to the reaction vessel. The reaction mixture was cooled to room temperature and then filtered to remove the insoluble polymeric quaternary ammonium catalyst which is now green in color. The yellow organic phase was separated from the filtrate and the organic solvent was stripped off. The residue was vacuum distilled to yield 50.27 grams of yellow oil with a boiling point of 95°–105° C. at 0.4 mm of Hg pressure. The yield of 2,6-di-t-butyl-4-allyl phenol was 82% of theory.

EXAMPLE II

Preparation of 2,6-di-t-butyl-4-allyl phenol with Quaternary Phosphonium Resin as the Triphase Catalyst A 1 liter, 3 neck flask equipped with a mechanical stirrer, thermometer, nitrogen inlet, dropping funnel and condenser was charged with 40 grams (1.0 mole) of sodium hydroxide and 50 ml. of H₂O. The NaOH was dissolved with stirring and the solution was cooled to 25° C. and then 100 ml. of toluene, 2.06 grams (0.01 moles) 2,6-di-t-butyl phenol and 6.25 grams ($\approx$0.006 moles) of S-X1 polystyrene quaternary phosphonium resin catalyst was charged into the reaction vessel. The dropping funnel was charged with a solution prepared from 49.44 grams (0.264 mole) of 2,6-di-t-butyl phenol, 32.0 grams (0.264 mole) of allyl bromide and 100 ml. of toluene. This solution was then added dropwise over a 40 minute period to the reaction vessel which had been heated to 50°–60° C. as stirring took place under a nitrogen blanket. After 3 hours of reaction time at 72° C. gas chromatographic analysis indicated that 50% of the starting materials had reacted to form 2,6-di-t-butyl-4-allyl phenol.

COMPARATIVE EXAMPLE III

Control With Unfunctionalized Resin

To demonstrate that quaternary functionalization of the resin is necessary for it to have catalytic activity the following experiment was performed.

The identical procedure to that performed in Example I was followed except that the S-X1 polystyrene quaternary ammonium resin was substituted with 6.4 grams of 2% cross-linked unfunctionalized polystyrene resin. Gas chromatographic analysis of the reaction mixture after 1½ hours at 72° C. showed none of the desired product.

EXAMPLE IV

To the reaction mixture, including unfunctionalized resin, of Example III which showed no formation of the desired product there was added the catalyst from Example I that was filtered from the reaction mixture after use therein. After 1 hour of reaction with the recycled catalyst, 50.5 grams of 2,6-di-t-butyl-4-allyl phenol was recovered. This demonstrates the recyclability of the catalyst.

Examples I through IV disclose and teach addition of the phenol/allyl halide solution to the reaction vessel. Experimentation has determined that the inverse method of addition of caustic to the phenol/allyl halide/catalyst gives comparable results.

INDUSTRIAL APPLICABILITY

The process of this invention provides a new and useful means to produce 2,6-di-t-alkyl-4-allyl phenols. In and of themselves 2,6-di-t-alkyl-4-allyl phenols are useful as antioxidants for organic materials but are also valuable as intermediates for other compounds. The process of this invention solves problems that heretofore had accompanied processes for the carbon alkylation of substituted phenols. Specifically, the process of this invention provides for recyclability of the catalyst, thus being ecologically and economically sound. In addition, the process of this invention provides for aqueous sodium hydroxide, a low-cost basic media, not normally effective in alkylations of this type.

While certain representative embodiments and details have been shown for the purpose of illustrating the invention, it will be apparent to those skilled in this art that various changes and modifications may be made therein without departing from the spirit or scope of the invention.

I claim:

1. A process wherein a 2,6di-tert-alkyl phenol of the structural formula:

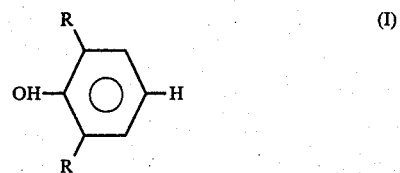

is reacted with an allyl halide of the structural formula:

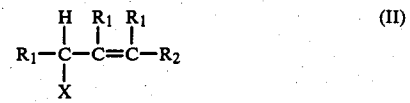

in the presence of an aqueous solution of an alkali metal hyroxide, a catalyst, and heat to yield a 2,6-di-tert-alkyl-4-alkenyl phenol of the structural formula:

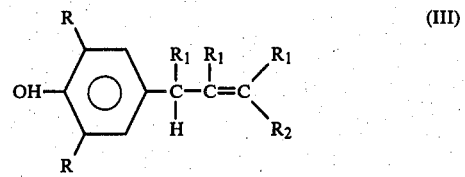

wherein R is a tertiary alkyl radical of 4 to 8 carbon atoms and R₁ is a monovalent radical selected from the group consisting of hydrogen, alkyl radicals of 1 to 6 carbon atoms; and R₂ is a monovalent radical selected from the group consisting of hydrogen, alkyl radicals of 1 to 6 carbon atoms and aryl radicals of 6 to 10 carbon atoms; and X is a chlorine or bromine radical, the improvement characterized in the use of a triphase catalyst defined by the formula:

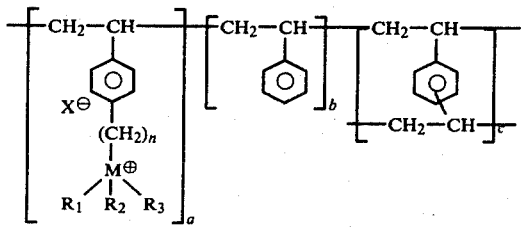

wherein the ratio of a to b pluc c may vary between 1 to 1 to 1 to 100 with a preferred range being 1 to 5 to 1 to 50 and wherein $R_1$, $R_2$ and $R_3$ are the same or different radicals selected from the group comprised of alkyl radicals of 1 to 12 carbon atoms, secondary alkyl radicals of 3 to 12 carbon atoms, cycloalkyl radicals of 5 to 8 carbon atoms; $X^{\ominus}$ is a radical selected from the group consisting of chlorine, fluorine and bromine and hydrogen sulfate radicals; M is phosphorus or nitrogen and n is equal to a whole positive integer from 1 to 12.

2. A process according to claim 1 wherein the 2,6-di-t-alkyl phenol is selected from the group consisting of 2,6-di-t-butyl phenol, 2,6-di-t-pentyl phenol, 2,6-di-t-hexyl phenol, 2,6-di-t-heptyl phenol and 2,6-di-t-octyl phenol.

3. A process according to claim 1 wherein the allylic halide is selected from the group consisting of:
allyl chloride
allyl bromide
crotyl chloride
crotyl bromide
methylallyl chloride
methylallyl bromide
cinnamyl chloride
cinnamyl bromide.

4. A process according to claim 1 wherein the alkali metal hydroxide is selected from the group consisting of sodium hydroxide, potassium hydroxide.

5. A process according to claim 1 wherein the concentration of the aqueous alkali metal hydroxide is 20–50 weight percent.

6. A process according to claim 1 wherein the reaction is conducted from 30° C. to 100° C.

* * * * *